United States Patent
Korman

(10) Patent No.: US 12,201,310 B2
(45) Date of Patent: *Jan. 21, 2025

(54) BURR TRAJECTORY GUIDE

(71) Applicant: WRIGHT MEDICAL TECHNOLOGY, INC., Memphis, TN (US)

(72) Inventor: Zachary Korman, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/600,851

(22) Filed: Mar. 11, 2024

(65) Prior Publication Data
US 2024/0206889 A1 Jun. 27, 2024

Related U.S. Application Data

(63) Continuation of application No. 17/653,526, filed on Mar. 4, 2022, now Pat. No. 11,957,364.

(60) Provisional application No. 63/167,878, filed on Mar. 30, 2021.

(51) Int. Cl.
*A61B 17/17* (2006.01)
*A61B 90/00* (2016.01)

(52) U.S. Cl.
CPC ........ *A61B 17/17* (2013.01); *A61B 2090/062* (2016.02)

(58) Field of Classification Search
CPC .......................... A61B 17/17; A61B 2090/062
See application file for complete search history.

(56) References Cited

U.S. PATENT DOCUMENTS 5,688,284 A * 11/1997 Chervitz ............ A61B 17/1714
606/88
2013/0325076 A1* 12/2013 Palmer ............... A61B 17/8635
606/104

(Continued)

FOREIGN PATENT DOCUMENTS

CN 211484785 U 9/2020
EP 1669034 B1 7/2008

(Continued)

OTHER PUBLICATIONS

Extended European Search Report issued in connection with Application No. 22160500.9, Jul. 28, 2022, 8 pages.

*Primary Examiner* — Kevin T Truong
*Assistant Examiner* — Diana Jones
(74) *Attorney, Agent, or Firm* — DUANE MORRIS LLP

(57) ABSTRACT

Provided is a guide assembly for guiding a bone cutting tool through a small incision in the skin near the bone that allows movement of the cutting tool in the bone in a wide angle while the cutting tool is rotated about a pivot point that is located at the small incision. The guide assembly includes a 2-piece construction that includes a guide component that holds the cutting tool and a track component having a semicircular arc shape on which the guide component is slidably engaged whereby sliding the guide component along the track component guides the movement of the cutting tool to rotate about a pivot point that is the center of curvature of the semicircular arc shape of the track component.

14 Claims, 10 Drawing Sheets

(56) References Cited

U.S. PATENT DOCUMENTS

| | | | |
|---|---|---|---|
| 2015/0031982 A1* | 1/2015 | Piferi | A61B 6/032 |
| | | | 600/417 |
| 2018/0242987 A1 | 8/2018 | Lintula et al. | |
| 2018/0242988 A1* | 8/2018 | Dacosta | A61B 17/1717 |
| 2020/0375436 A1 | 12/2020 | Kielack et al. | |

FOREIGN PATENT DOCUMENTS

| | | |
|---|---|---|
| EP | 3744270 B1 | 4/2022 |
| WO | 2020180598 A1 | 9/2020 |

\* cited by examiner

BURR TRAJECTORY GUIDE

CROSS-REFERENCE TO RELATED APPLICATIONS

This application is a continuation of U.S. patent application Ser. No. 17/653,526, filed Mar. 4, 2022, which claims priority under 35 U.S.C. § 119(e) to U.S. Provisional Application No. 63/167,878, filed Mar. 30, 2021, the entireties of which are incorporated herein by reference.

FIELD

This disclosure relates generally to a surgical instrument for guiding the trajectory of a burr tool.

BACKGROUND

Currently, making an osteotomy of a bone such as the first metatarsal through an incision in a minimally invasive surgical procedure is carried out using a handheld cutting tool, such as a burr, and relies solely on the skill of the surgeon to keep the cutting tool within the intended cutting plane as the cutting tool is advanced through the target bone. Thus, it would be helpful to have a guiding jig that can ensure that a handheld cutting tool is guided through the target bone within the intended cutting plane while minimizing excess forces being exerted on the soft tissue and without solely relying on the surgeon's skill.

SUMMARY

Provided is a guide assembly for guiding a bone cutting tool through a small incision in the skin near the bone that allows movement of the cutting tool in the bone in a wide angle while the cutting tool is rotated about a pivot point that is located at the small incision. The guide assembly includes a 2-piece construction that includes a guide component that holds the cutting tool and a track component having a semicircular arc shape on which the guide component is slidably engaged whereby sliding the guide component along the track component guides the movement of the cutting tool to rotate about a pivot point that is the center of curvature of the semicircular arc shape of the track component. By aligning the pivot point to the incision in the skin the cutting tool can be moved through the target bone making the cut through the cutting plane while maintaining the shaft of the cutting tool to stay within the incision because the pivot point is within the incision. This allows the incision to be as minimal as possible and reduce the frequency of skin irritation or heat damage. Such guide assembly would be ideal for use in minimally invasive surgical procedures.

In some embodiments the guide assembly comprises a track component comprising a track, and a guide component slidably attached to the track component, where the guide component comprises a guide hole extending through the guide component for receiving a tool. The guide hole defines a longitudinal axis through the guide component. The guide component is slidable along the track, where the track defines a semicircular arc path for the guide component and the semicircular arc path defines a center of curvature. The guide hole is oriented in the guide component so that the longitudinal axis intersects the center of curvature, whereby when the tool is inserted through the guide hole of the guide component, the tool's longitudinal axis is coaxially aligned with the longitudinal axis of the guide hole so that when the tool is extended beyond the center of curvature, the tool intersects the center of curvature regardless of the guide component's position along the track.

Also provided is a method of performing an osteotomy in a target bone using the guide assembly of the present disclosure.

BRIEF DESCRIPTION OF THE DRAWINGS

These and other features and advantages of the bone fixation implants and methods of implantation described herein will be more fully disclosed in, or rendered obvious by, the following detailed description of the preferred embodiments, which is to be considered together with the accompanying drawings wherein like numbers refer to like parts and further wherein:

FIG. 1A is a perspective view of the guide assembly secured to a bone, FIG. 1B is a perspective view of the guide assembly secured to the bone seen from a different angle, and FIG. 1C is an exploded view of the guide assembly of FIGS. 1A and 1B showing the track component and the guide component.

FIG. 2A is a perspective view of the guide assembly secured to a bone, FIG. 2B is a perspective view of the guide assembly secured to the bone seen from a different angle, and FIG. 2C is an exploded view of the guide assembly of FIGS. 2A and 2B showing the track component and the guide component.

FIG. 3A is a perspective view of the guide assembly secured to a bone, FIG. 3B is a perspective view of the guide assembly secured to the bone viewed from a different angle, FIG. 3C is an exploded view of the guide assembly of FIGS. 3A and 3B showing the track component and the guide component.

Figure 1A:
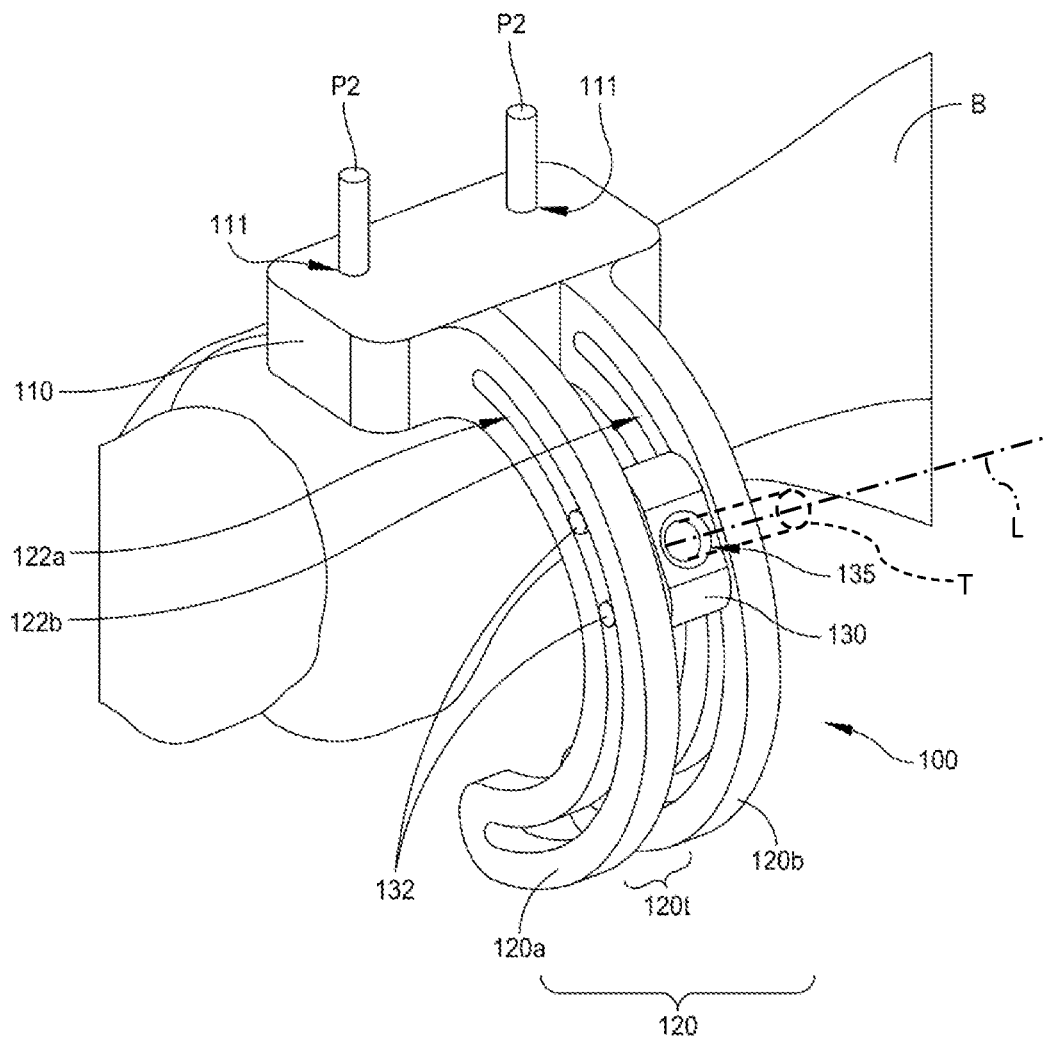
FIGS. 1A-1C are illustrations of a guide assembly according to another embodiment, where

All illustrations shown in the figures are schematic and are not intended to show actual dimensions or proportions.

DETAILED DESCRIPTION

This description of preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 1B:
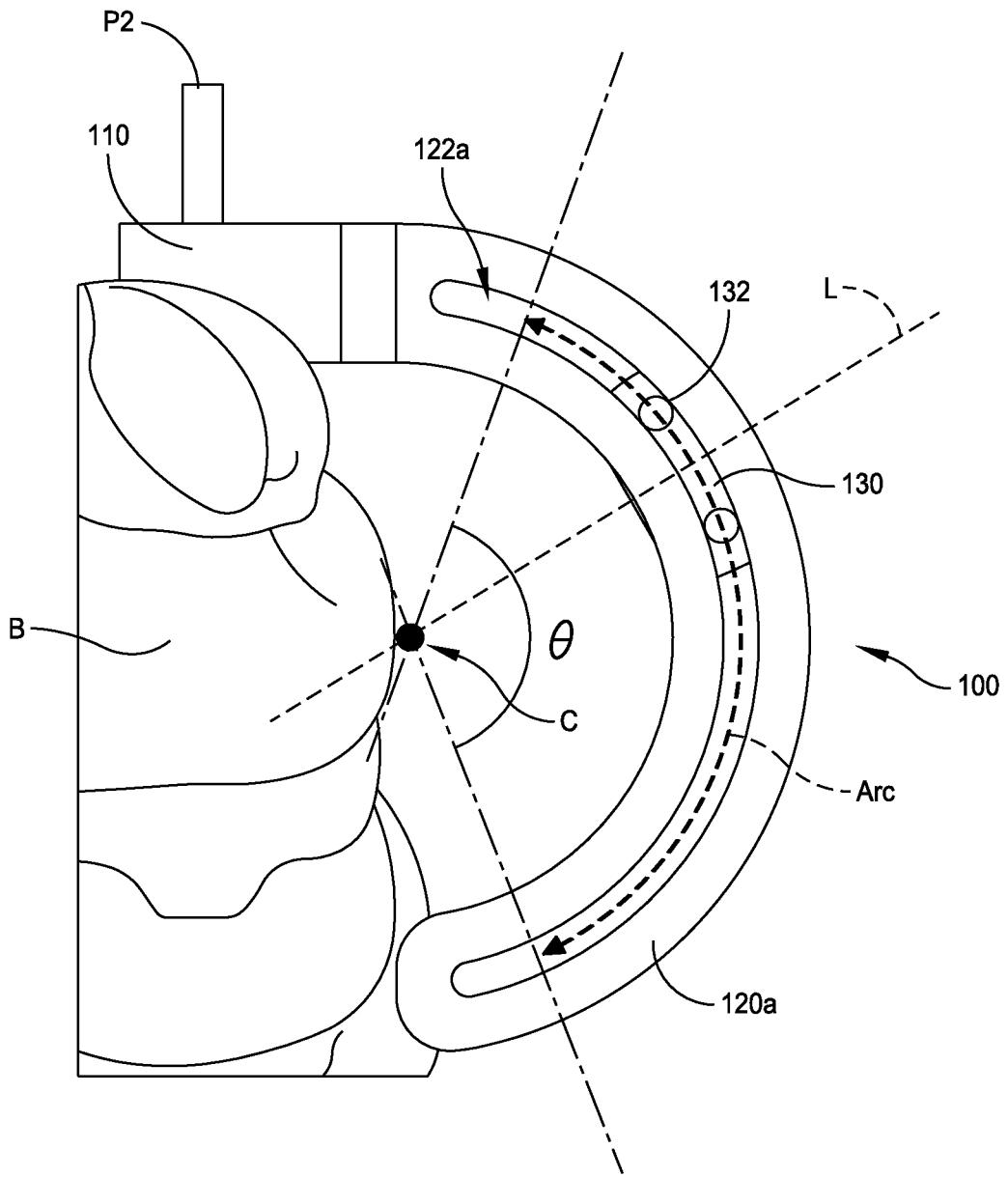
Figure 1C:
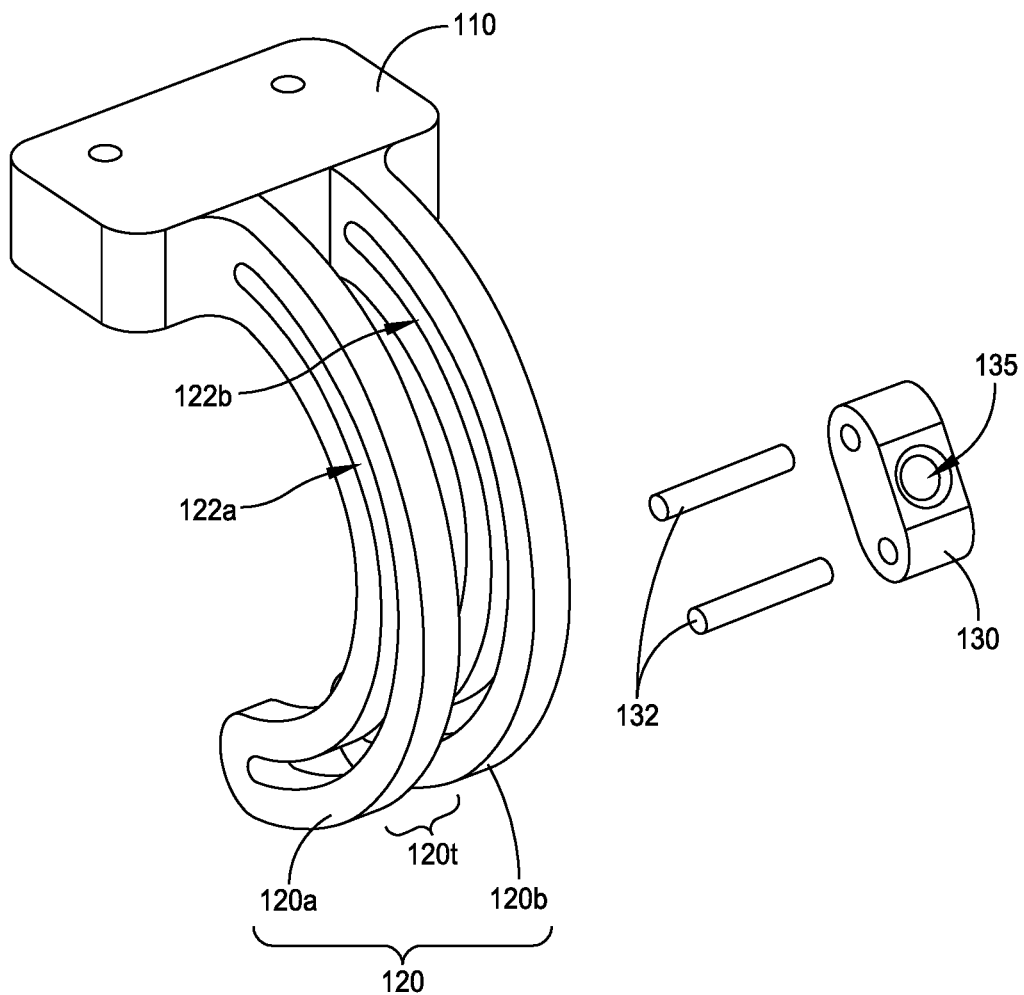

Referring to FIGS. 1A-1B, disclosed is a guide assembly 100 for guiding a tool T, such as a cutting tool, during a surgical procedure, such as an osteotomy, using the tool to cut a target bone B. The guide assembly 100 comprises a body 110, a track component 120 extending from the body, and a guide component 130. The guide component is slidably attached to the track component. The track component comprises a track 120t and the guide component 130 is slidable along the track 120t.

The track component 120 is configured to define a semicircular shape for the track 120t and thus the track defines a semicircular arc path Arc for the guide component 130 that slides on the track. The semicircular arc path Arc defines a center of curvature C.

In this embodiment, the track component 120 comprises two rails 120a, 120b extending from the body 110 that are curved in semicircular curvature and are arranged parallel to each other to form the track 120t. The guide component 130 slides in the track 120t between the two rails 120a, 120b. Each of the two rails 120a, 120b comprises a slot 122a, 122b, respectively, that extend along a substantial portion of the rails 120a, 120b. The guide component 130 comprises two or more bosses 132 that extend into the slots 122a, 122b and enable the guide component 130 to slide within the track 120t by following the slots 122a, 122b. In some embodiments, the bosses 132 can be roller bearings that ride in the slots 122a, 122b. Roller bearings would provide smoother frictionless sliding motion for the guide component 130. In some embodiments, the bosses 132 can be simple dowel pins or low-friction bushings. In all of the embodiments, the surface finish of the contacting surfaces on the bosses and the corresponding slots 122a, 122b would be appropriately selected to minimize the friction.

The guide component 130 comprises a guide hole 135 extending through the guide component for receiving the cutting tool T. The guide hole 135 defines a longitudinal axis L through the hole. The cutting tool T can be a burr, a drill bit, or other cutting instrument depending on the needs of a particular cutting procedure. The cutting tool T should be of the size and dimension that can fit through the guide hole 135.

The guide hole 135 is oriented in the guide component 130 so that the longitudinal axis L intersects the center of curvature C of the semicircular arc path. Thus, when a cutting tool is inserted through the guide hole 135, the longitudinal axis of the tool is coaxial with the longitudinal axis L of the guide hole. Because of this configuration, when the guide assembly 100 is positioned and attached to the target bone B near the incision made in the skin next to the location in the target bone B with the center of curvature C aligned and located at the incision (see FIG. 3D), and the cutting tool is inserted through the guide hole and extended through the incision and driven into the bone B, sliding the guide component 135 along the semicircular arc path Arc defined by the track 120t will sweep the cutting tool through a cutting plane Pguide defined by the guide assembly. This is schematically illustrated in FIG. 3D in which the guide assembly embodiment 300 is used as an example.

Therefore, by positioning and affixing the guide assembly 100 to a portion of the target bone B so that the cutting plane Pguide defined by the guide assembly is aligned to the intended cutting plane in the target bone B and that the center of curvature C of the semicircular arc path Arc is located where the skin incision is made, the guide assembly ensures that the cutting tool placed through the guide hole 135 and extended through the center of curvature C and beyond into the target bone B will always rotate about the skin incision. This allows the incision to be as small as possible. This would be beneficial for minimally invasive surgical procedures.

The body 110 of the guide assembly can comprise two or more holes 111 for receiving fixation pins P1, P2, e.g. K-wires, for affixing the guide assembly 100 to the target bone B. However, any reasonable method of affixing the guide assembly to the bone is acceptable (i.e., adhesive, attachment to a brace around a neighboring bone, etc.). This is true for any of the embodiments of the guide assembly disclosed herein.

Figure 2A:
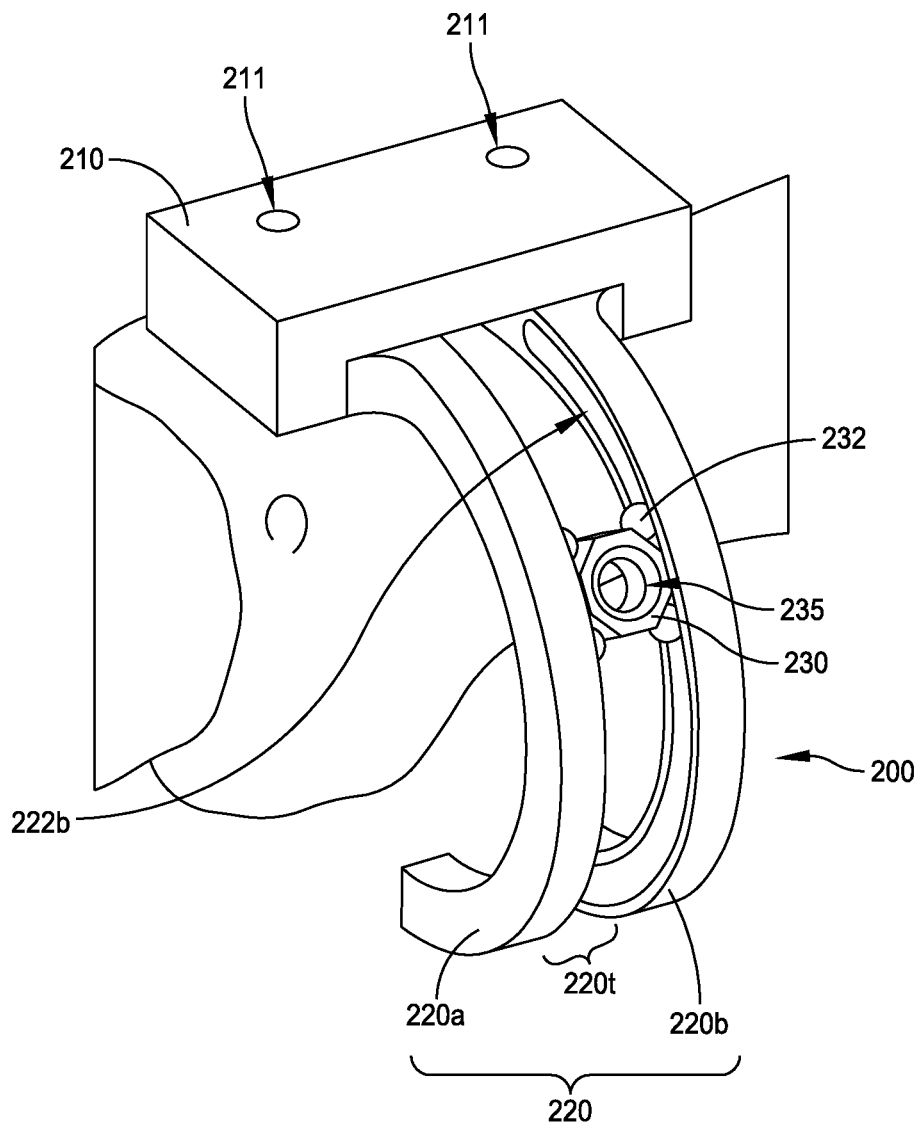
FIGS. 2A-2C are illustrations of a guide assembly according to another embodiment, where
Figure 2B:
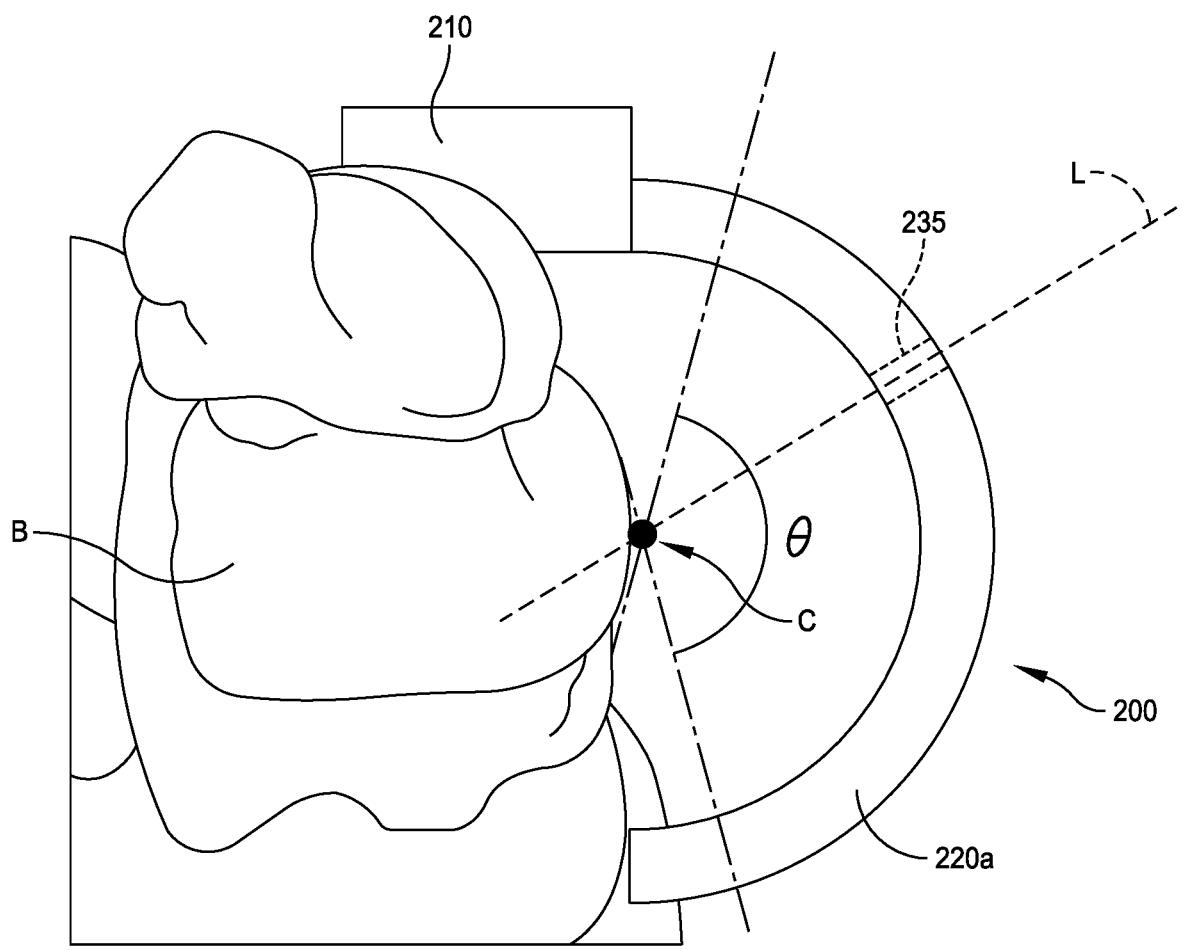
Figure 2C:
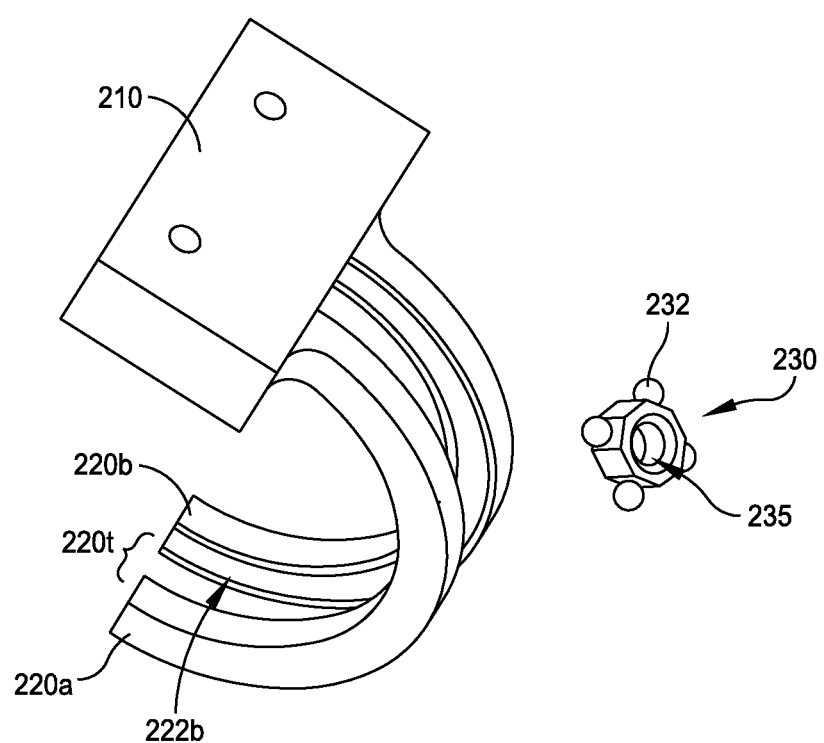

FIGS. 2A-2B are illustrations of another embodiment of a guide assembly 200 for guiding a tool T, such as a cutting tool during a surgical procedure for cutting a bone. The guide assembly 200 comprises a body 210, a track component 220 extending from the body, and a guide component 230. The guide component is slidably attached to the track component. The track component comprises a track 220t and the guide component 230 is slidable along the track 220t.

The track component 220 is configured to define a semicircular shape for the track 220t and thus the track defines a semicircular arc path Arc for the guide component 230 that slides on the track. The semicircular arc path Arc defines a center of curvature C.

In this embodiment, the track component 220 comprises two rails 220a, 220b extending from the body 210 that are curved in semicircular curvature and are arranged parallel to each other to form the track 220t. The guide component 230 slides in the track 220t between the two rails 220a, 220b. Each of the two rails 220a, 220b comprises a slot 222a, 222b, respectively, that extend along a substantial portion of the rails 220a, 220b. The guide component 230 comprises two or more spherical bearings or styli 232 that extend into the slots 222a, 222b and enable the guide component 230 to slide within the track 220t by following the slots 222a, 222b.

The guide component comprises a guide hole 235 extending through the guide component for receiving the cutting tool. The guide hole 235 defines a longitudinal axis L through the hole. The cutting tool can be a burr, a drill bit, or other cutting instrument depending on the needs of a particular cutting procedure.

The guide hole 235 is oriented in the guide component 230 so that the longitudinal axis L intersects the center of curvature C of the semicircular arc path. Because of this configuration, when the cutting tool is inserted through the guide hole of the guide component so that the tool's longitudinal axis is coaxially aligned with the longitudinal axis L of the guide hole, and the cutting tool is extended beyond the center of curvature C, the shaft portion of the cutting tool intersects the center of curvature C regardless of the guide component's position along the track 220t.

Therefore, by positioning and affixing the guide assembly 200 to a portion of the target bone B so that the cut plane Pguide defined by the guide assembly is aligned to the intended cutting plane in the target bone B and that the center of curvature C of semicircular arc path is located where the MIS skin incision made, the guide assembly ensures that the cutting tool placed through the guide hole 235 and extended through the center of curvature C and beyond into the target bone B will always rotate about the skin incision. This allows the incision to be as small as possible. The concept of the cut plane Pguide is illustrated in FIG. 3D using the guide assembly 300.

The body 210 of the guide assembly can comprise two or more holes 211 for receiving fixation pins P1, P2, e.g. K-wires, for affixing the guide assembly 200 to the target bone B.

FIGS. 3A-3D are illustrations of another embodiment of a guide assembly 300 for guiding a tool T, such as a cutting tool during a surgical procedure for cutting a bone. The guide assembly 300 comprises a body 310, a track component 320 extending from the body, and a guide component 330. The guide component is slidably attached to the track component. The track component 320 functions as a track for the guide component 330 to slide along.

The track component 320 is configured with a semicircular arc shape and thus defines a semicircular arc path Arc for the guide component 330 that slides on the track. The semicircular arc path Arc defines a center of curvature C.

Figure 3A:
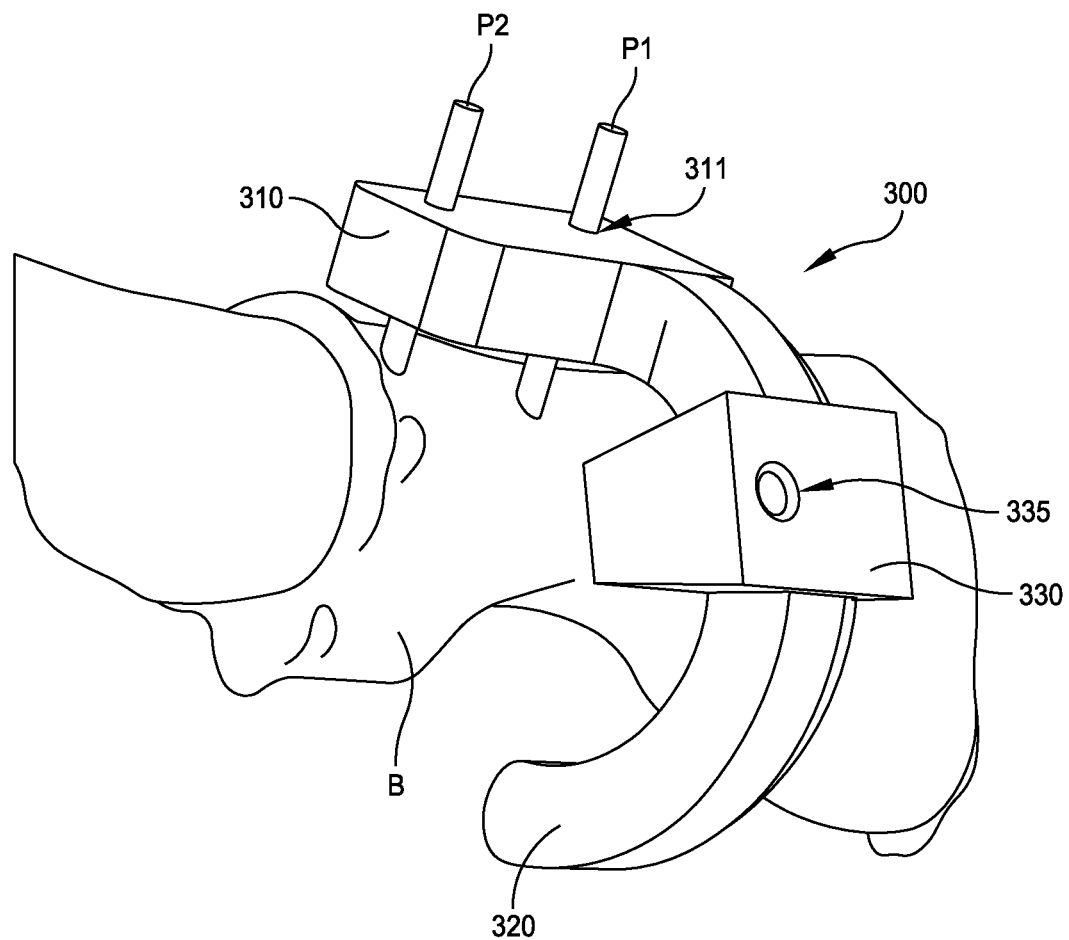
FIGS. 3A-3D are illustrations of a guide assembly according to another embodiment, where
Figure 3B:
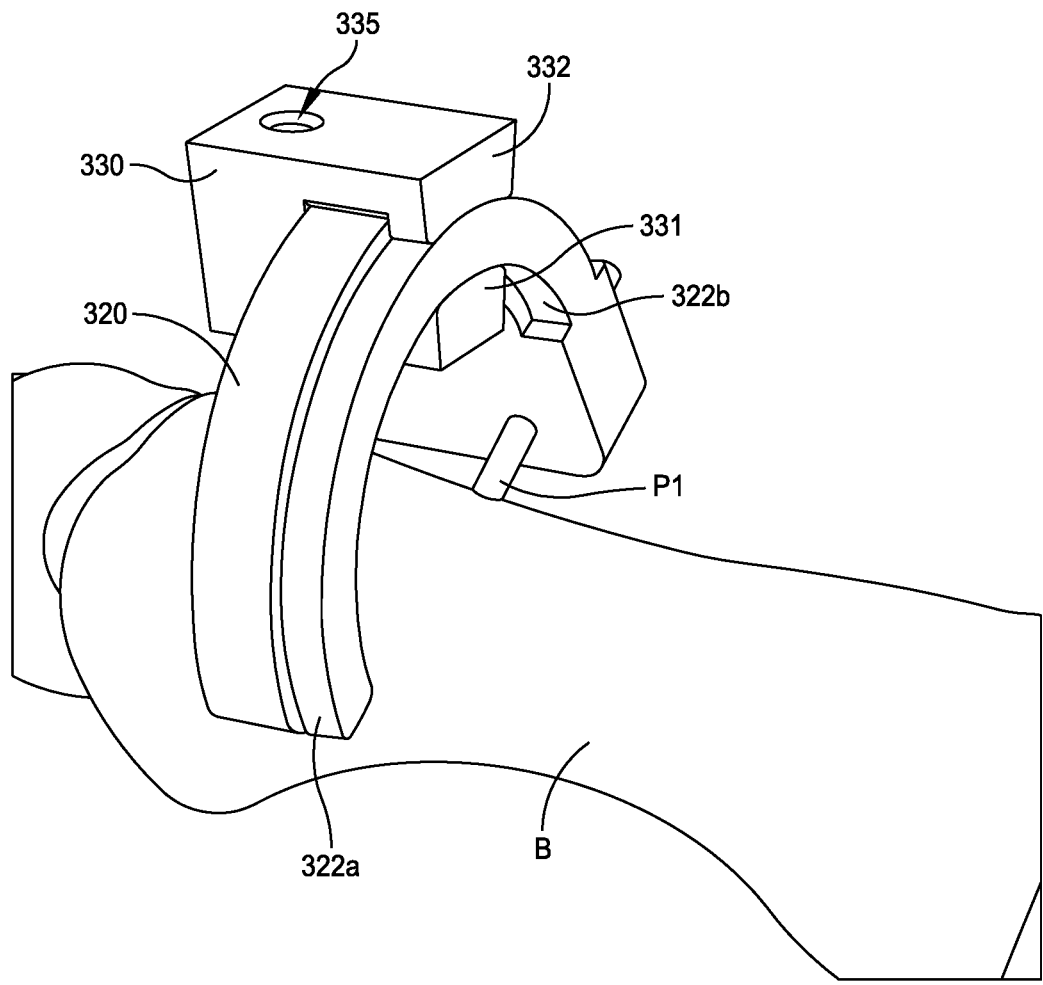
Figure 3C:
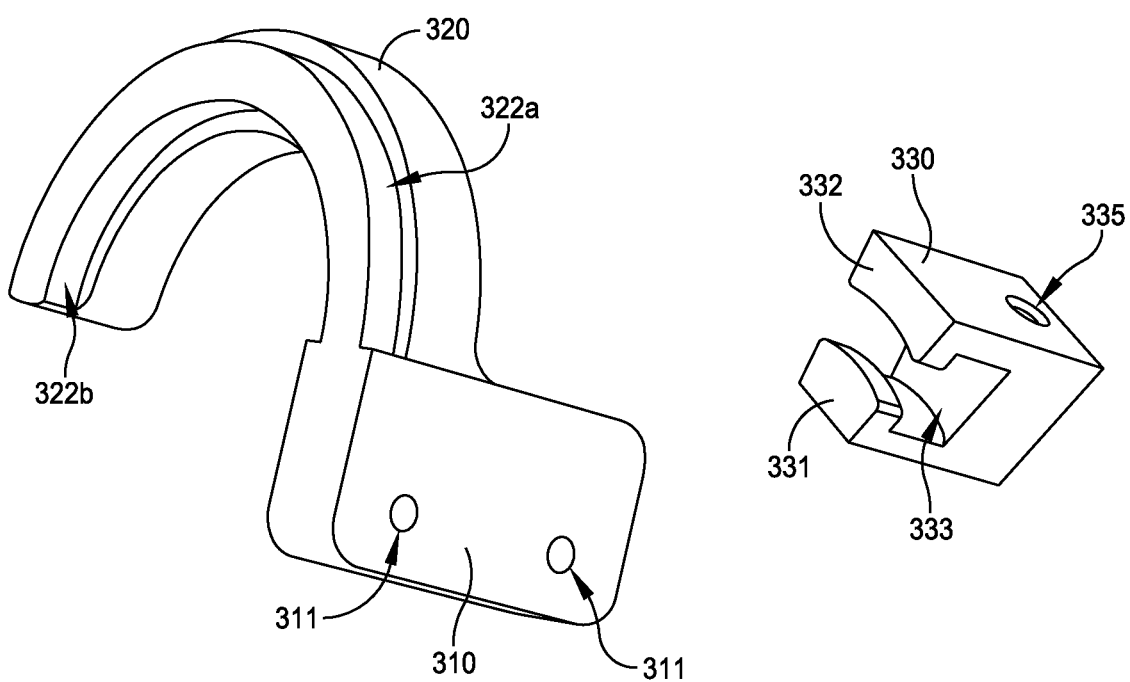
Figure 3D:
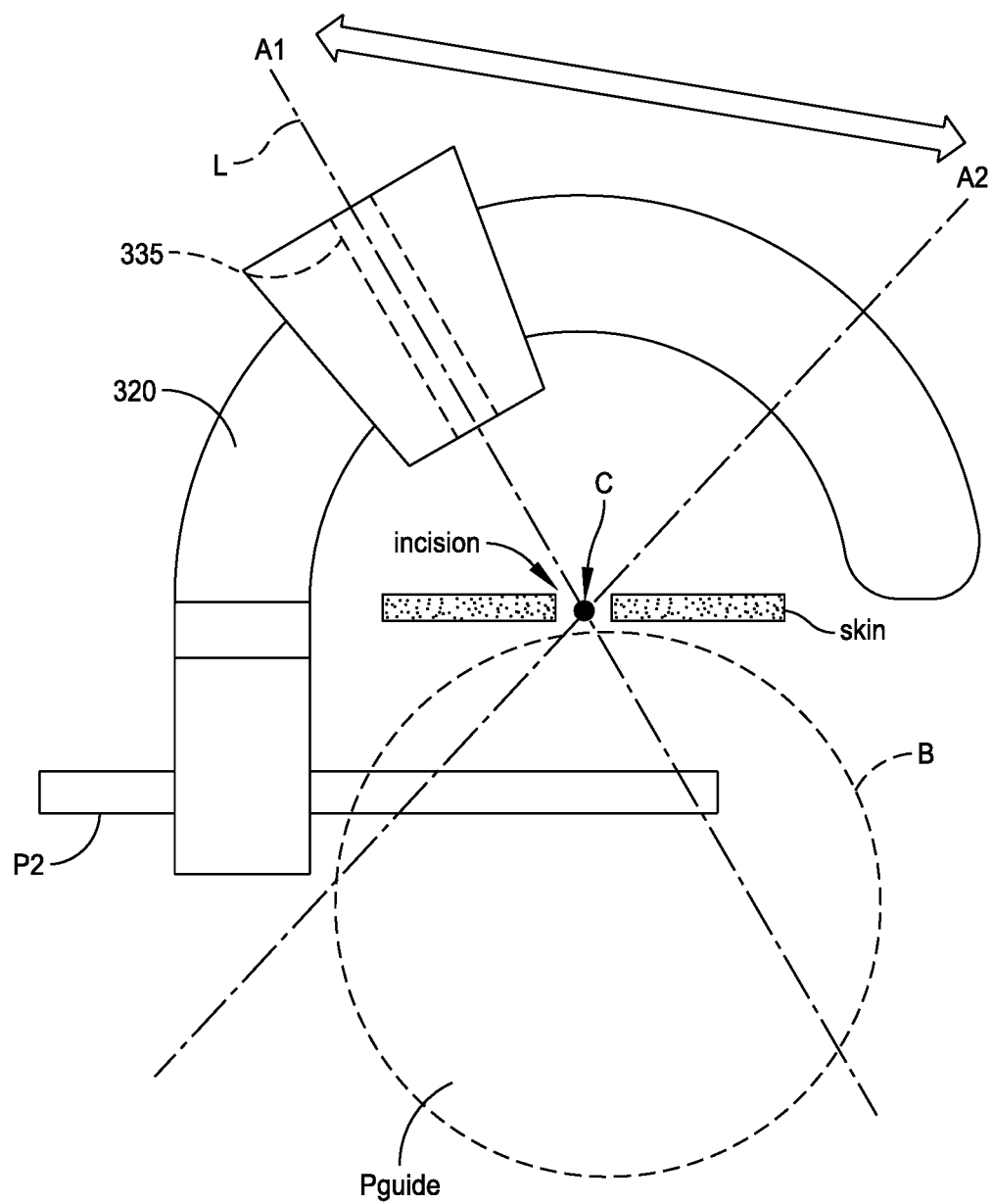

Referring to FIGS. 3B-3D, the track component 320 comprises two ledges 322a, 322b extending along the track component 320 in the semicircular arc shape and defining the track. The guide component 330 comprises a recess 333 through which the track component 320 extends so that the guide component 330 can slide along the track component 320. The guide component 330 comprises two bosses 331, 332 that are complementary to and follow the two ledges 322a, 322b and keep the guide component 330 engaged to the track component 320. Thus, the two bosses enable the guide component to slidably engage the track by engaging the two ledges.

The guide component comprises a guide hole 335 extending through the guide component for receiving the cutting tool. The guide hole 335 defines a longitudinal axis L through the hole. The cutting tool can be a burr, a drill bit, or other cutting instrument depending on the needs of a particular cutting procedure. The guide hole in the guide component is positioned next to the track component.

The guide hole 335 is oriented in the guide component 330 so that the longitudinal axis L intersects the center of curvature C of the semicircular arc path. Because of this configuration, when the cutting tool is inserted through the guide hole of the guide component so that the tool's longitudinal axis is coaxially aligned with the longitudinal axis L of the guide hole, and the cutting tool is extended beyond the center of curvature C, the shaft portion of the cutting tool intersects the center of curvature C regardless of the guide component's position along the track component 320.

Therefore, by positioning and affixing the guide assembly 300 to a portion of the target bone B so that the cut plane Pguide defined by the guide assembly is aligned to the intended cutting plane in the target bone B and that the center of curvature C of semicircular arc path is located where the MIS skin incision made, the guide assembly ensures that the cutting tool placed through the guide hole 335 and extended through the center of curvature C and beyond into the target bone B will always rotate about the skin incision. This allows the incision to be as small as possible. The concept of the cut plane Pguide is illustrated in FIG. 9 using the guide assembly 300.

The body 310 of the guide assembly can comprise two or more holes 311 for receiving fixation pins P1, P2, e.g. K-wires, for affixing the guide assembly 300 to the target bone B.

As illustrated by the examples of the guide assemblies 100, 200, and 300 disclosed herein, the sliding interface between the track component 120, 220, 320 and the guide component 130, 230, 330 can be accomplished by a variety of other mechanisms and are not limited to the three examples illustrated herein. What is required in all embodiments is that the track component be configured to provide a semicircular arc path Arc for the guide component to move/slide along a portion of the track component and that the guide component is configured with a guide hole for a tool, where the guide hole's longitudinal axis points toward the center of curvature C of the semicircular arc path Arc no matter where along the semicircular arc path the guide component is.

In some embodiments of the guide assembly, the track component 120, 220, 320 can be configured to be secured to a patient at a point along the length of a long bone.

Referring to FIG. 1B, in some embodiments of the guide assembly, the length of the semicircular arc path Arc for the guide component 130, 230, 330 that is provided by the track component 120, 220, 320 is defined by the indicated central angle θ. The guide assemblies 100, 200, 300 can be configured to provide a central angle θ that is about 90 degrees and up to 180 degrees. The central angle θ is the maximum angle the longitudinal axis L of the guide component 130, 230, 330 can sweep from the position of the guide component 130, 230, 330 at one end of the track component 120, 220, 320 to the position of the guide component 130, 230, 330 at the opposite end of the track component 120, 220, 320. The central angle θ defines the maximum range of the angular movement of the guiding component 130, 230, 330.

Method

According to another aspect, a method of using the guide assembly 100, 200, 300 comprises (a) making an incision in the skin next to the site of the intended osteotomy in the target bone and creating a working space under the skin; (b) attaching a guide assembly 100, 200, 300 with anchor wires (such as K-wires) such that the center of curvature C of the guide assembly is close to the incision; (c) inserting a cutting tool (such as a burr or burr handle) into the guide hole 135, 235, 335 in the guide component 130, 230, 330; (d) inserting the cutting tool through the incision and driving the cutting tool into the target bone under power until it reaches a desired depth; and (e) rotating the cutting tool up or down about the center of curvature C guided by sliding of the guiding component along the track component to make a desired cut in the target bone. In some situations, the desired depth reached with the cutting tool in step (d) can be completely through the bone until the cutting tool penetrates the far-side cortex. The desired cut made in the target bone in step (e) can be a full cut or a partial cut through the target bone.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the claimed devices, kits, systems, and methods.

I claim:

1. A guide assembly comprising:
 a body configured to be secured to a long bone;
 a track component extending from a portion of the body, including two spaced-apart parallel curved rails, each rail having one end secured to the body and one end spaced-away from the body and unsecured to the long bone and a slot that extends along a substantial portion of the rail to form a track from the body to the spaced-away unsecured end; and
 a guide component including bearings that is positioned between the two parallel curved rails with at least one bearing positioned within each slot of the two spaced-apart parallel curved rails so as to be constrained by the track component, wherein the guide component comprises a guide hole for receiving a tool, the guide hole defining a longitudinal axis therethrough,
wherein the guide component is arranged and configured to move along the track from the body to the spaced-away unsecured end,
wherein the track defines a curved arc path for the guide component and a center of curvature, and
wherein the guide hole is oriented in the guide component so that the longitudinal axis intersects the center of curvature, whereby when the tool is inserted through the guide hole of the guide component, the tool's longitudinal axis is coaxially aligned with the longitudinal axis of the guide hole so that when the tool is extended beyond the center of curvature, the tool intersects the center of curvature regardless of the guide component's position along the track from the body to the spaced-away unsecured end.

2. The guide assembly of claim 1, wherein the track component is configured to be secured to a patient at a point along a length of the long bone.

3. The guide assembly of claim 1, wherein the curved arc path can have a central angle θ, wherein 90 degrees≤θ≥180 degrees.

4. The guide assembly of claim 1, wherein the guide component comprises two or more roller bearings rotatably engaging the two spaced-apart parallel curved rails, wherein the two or more roller bearings provide a rolling engagement with the two spaced-apart parallel curved rails of the track.

5. The guide assembly of claim 1, wherein the track component is configured with a semicircular arc shape and two ledges extending in the semicircular arc shape defining the track for receiving the roller bearings.

6. The guide assembly of claim 1, wherein the guide hole in the guide component is positioned next to the track component.

7. The guide assembly of claim 1, wherein the tool is a burr, a drill bit, or other cutting instrument that can fit through the guide hole.

8. A method of performing an osteotomy in a target bone using a guide assembly that comprises:
a body configured to be secured to a long bone;
a track component extending from a portion of the body, including two spaced-apart parallel curved rails, each rail having one end secured to the body and one end spaced-away from the body and unsecured to the long bone and a slot that extends along a substantial portion of the rail to form a track from the body to the spaced-away unsecured end; and
a guide component including bearings is positioned between the two spaced-apart parallel curved rails with at least one bearing positioned within each slot of the two spaced-apart parallel curved rails so as to be constrained by the track component, wherein the guide component comprises a guide hole for receiving a tool, the guide hole defining a longitudinal axis therethrough,
wherein the guide component is arranged and configured to move along the track from the body to the spaced-away unsecured end,
wherein the track defines a curved arc path for the guide component and a center of curvature, and
wherein the guide hole is oriented in the guide component so that the longitudinal axis intersects the center of curvature, whereby when the tool is inserted through the guide hole of the guide component, the tool's longitudinal axis is coaxially aligned with the longitudinal axis of the guide hole so that when the tool is extended beyond the center of curvature, the tool intersects the center of curvature regardless of the guide component's position along the track from the body to the spaced-away unsecured end;
the method comprising:
(a) making an incision in skin next to a site of the intended osteotomy in the target bone;
(b) attaching the guide assembly with one or more anchor wires such that the center of curvature of the guide assembly is close to the incision;
(c) inserting the tool into the guide hole in the guide component;
(d) inserting the tool through the incision and driving the cutting tool into the target bone under power until it reaches a desired depth; and
(e) rotating the tool up or down about the center of curvature guided by sliding of the guiding component along the track component.

9. The method of claim 8, wherein the tool is a burr, a drill bit, or other cutting instrument that can fit through the guide hole.

10. A guide assembly comprising:
a body configured to be secured to a long bone;
a track component extending from a portion of the body, including two spaced-apart parallel curved rails, each rail having one end secured to the body and one end spaced-away from the body and unsecured to the long bone and a curved groove extending in an arc along a substantial portion of each rail to form a track from the body to the spaced-away unsecured end; and
a guide component including a plurality of spherical styli arranged to extend into the two curved grooves, wherein the plurality of spherical styli provide a slidable engagement when the guide component is positioned between the two parallel curved rails with at least one spherical styli positioned within each groove, wherein the guide component comprises a guide hole for receiving a tool, the guide hole defining a longitudinal axis therethrough,
wherein the guide component is arranged and configured to move along the track from the body to the spaced-away unsecured end,
wherein the track defines a curved arc path for the guide component and a center of curvature, and
wherein the guide hole is oriented in the guide component so that the longitudinal axis intersects the center of curvature, whereby when the tool is inserted through the guide hole of the guide component, the tool's longitudinal axis is coaxially aligned with the longitudinal axis of the guide hole so that when the tool is extended beyond the center of curvature, the tool intersects the center of curvature regardless of the guide component's position along the track from the body to the spaced-away unsecured end.

11. The guide assembly of claim 10, wherein the track component is configured to be secured to a patient at a point along a length of the long bone.

12. The guide assembly of claim 10, wherein the curved arc path can have a central angle θ, wherein 90 degrees≤θ≥180 degrees.

13. The guide assembly of claim 10, wherein the track component is configured with a semicircular arc shape and two ledges extending in the semicircular arc shape defining the track.

14. The guide assembly of claim 10, wherein the tool is a burr, a drill bit, or other cutting instrument that can fit through the guide hole.

\* \* \* \* \*